United States Patent [19]

Pommer et al.

[11] 3,993,772

[45] Nov. 23, 1976

[54] CERTAIN N-METHOXY-N-CYCLOALKYL-2-METHYL-3-FURANCARBOXAMIDES AND FUNGICIDAL METHOD USING SAME

[75] Inventors: Ernst-Heinrich Pommer, Limburgerhof; Bernd Zeeh; Friedrich Linhart, both of Ludwigshafen, all of Germany

[73] Assignee: BASF Aktiengesellschaft, Ludwigshafen (Rhine), Germany

[22] Filed: Nov. 4, 1975

[21] Appl. No.: 628,801

[30] Foreign Application Priority Data
Nov. 21, 1974 Germany............................ 2455082

[52] U.S. Cl.............................. 424/285; 260/347.3
[51] Int. Cl.²...................................... C07D 307/68
[58] Field of Search................... 260/347.3; 424/285

[56] References Cited
UNITED STATES PATENTS

| | | | |
|---|---|---|---|
| 3,778,512 | 12/1973 | Krenzer et al. | 424/285 |
| 3,806,506 | 4/1974 | Felauer et al. | 260/347.3 |
| 3,862,966 | 1/1975 | Distler et al. | 260/347.3 |

FOREIGN PATENTS OR APPLICATIONS 2,019,535   11/1971   Germany

Primary Examiner—Henry R. Jiles
Assistant Examiner—Bernard Dentz
Attorney, Agent, or Firm—Johnston, Keil, Thompson & Shurtleff

[57] ABSTRACT

New and valuable furanhydroxamic acid derivatives having a good fungicidal action, fungicides containing these compounds as active ingredients, a process for controlling the growth of fungi with these compounds, and a process for their manufacture.

5 Claims, No Drawings

CERTAIN N-METHOXY-N-CYCLOALKYL-2-METHYL-3-FURANCARBOXAMIDES AND FUNGICIDAL METHOD USING SAME

The present invention relates to new and valuable furanhydroxamic acid derivatives, their manufacture, and their use as fungicides.

It is known that amides of furancarboxylic acids may be used as fungicidal active ingredients (German Laid-Open Application DOS No. 2,019,535); however, the action of these compounds is unsatisfactory.

We have now found that furanhydroxamic acid derivatives of the formula

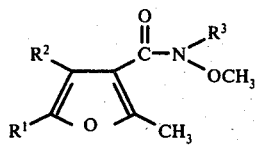

where $R^1$ is hydrogen or methyl, $R^2$ is hydrogen or methyl, and $R^3$ is cyclopentyl or cyclohexyl, have a better fungicidal action in crop plants than the prior art compounds.

The following compounds are examples of compounds according to the invention:

O-methyl-N-cyclopentyl-2-methylfuran-3-hydroxamic acid
O-methyl-N-cyclohexyl-2-methylfuran-3-hydroxamic acid
O-methyl-N-cyclopentyl-2,4-dimethylfuran-3-hydroxamic acid
O-methyl-N-cyclohexyl-2,4-dimethylfuran-3-hydroxamic acid
O-methyl-N-cyclopentyl-2,5-dimethylfuran-3-hydroxamic acid
O-methyl-N-cyclohexyl-2,5-dimethylfuran-3-hydroxamic acid
O-methyl-N-cyclopentyl-2,4,5-trimethylfuran-3-hydroxamic acid
O-methyl-N-cyclohexyl-2,4,5-trimethylfuran-3-hydroxamic acid.

The compounds of the invention are obtained from hydroxamic acids of the formula

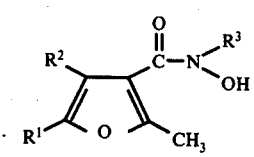

by reaction with a methylating agent such as dimethyl sulfate either without solvent or in one of the conventional organic solvents or in water, and in the presence or absence of a base such as triethylamine, sodium hydrogen carbonate, sodium carbonate and sodium hydroxide.

The new hydroxamic acids of the formula II may be obtained by reaction of compounds of the formula

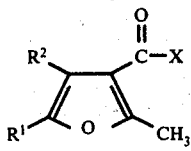

where $R^1$ and $R^2$ have the above meanings and X denotes halogen, with a compound of the formula

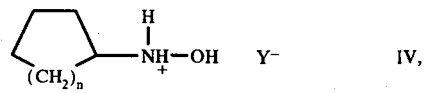

where $n$ denotes one of the integers 1 and 2 and $Y^-$ denotes the anion of any inorganic or organic acid, e.g., hydrochloric acid, hydrobromic acid, nitric acid, phosphoric acid, acetic acid, formic acid, propionic acid, benzoic acid, etc., in a solvent such as benzene, tetrahydrofuran, dioxane, methylene chloride, chloroform and water, and in the presence of an organic or inorganic base, e.g., triethylamine, sodium hydrogen carbonate, sodium carbonate, sodium hydroxide, etc.

Compounds III and IV may be prepared by conventional methods: Beilstein's Handbuch der Organischen Chemie, 18, II 271; Ya. Kastron, G. Veinbergs, R. Gavars and S. Hillers, Khim. Geterotsikl. Soedin., 2, 863 (English 657), 1966; H. Gilman and R. R. Burtner, Rec. trav. chim., 51, 667, 1932; U.S. Pat. No. 3,470,151; C.A., 72: P 21 682 a.

The following examples demonstrate the preparation of the new furanhydroxamic acids and their derivatives, without their being restricted thereto.

EXAMPLE 1

57 parts (by weight) of N-cyclohexylhydroxylamine hydrochloride is added to 800 parts of benzene; 71 parts of triethylamine is then introduced into this mixture. After the mixture has been stirred for 1 hour, a solution of 50 parts of 2-methylfuran-3-carboxylic chloride in 100 parts of benzene is dripped in at room temperature. After the mixture has been stirred for 3 hours the precipitate is filtered and washed with benzene. The filtrate is washed with water, dried over sodium sulfate and evaporated. The crystalline residue is recrystallized from cyclohexane. There is obtained 33 parts of N-cyclohexyl-2-methylfuran-3-hydroxamic acid, m.p.: 108°–110° C.

The compound has the following structural formula:

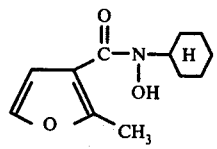

22.5 Parts of this compound is dissolved in 250 parts of dichloromethane; 12 parts of sodium hydroxide dissolved in 50 parts of water is then added to this solution. 14 parts of dimethyl sulfate is then dripped into this solution and the whole is stirred for 5 hours. The organic phase is separated, dried over anhydrous sodium sulfate and evaporated. The oil which remains is purified by column chromatography over silica gel with a 1:1 mixture of cyclohexane and ethyl acetate as developer. After the eluate has been evaporated, a distillable oil remains which soon solidifies. There is obtained 15.8 parts of O-methyl-N-cyclohexyl-2-methylfuran-3-hydroxamic acid; m.p.: 46° C; b.p. (0.01 mm): 119° C.

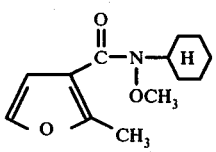

EXAMPLE 2

16.6 Parts of N-cyclohexylhydroxylamine hydrochloride is added to 300 parts of benzene; 20.2 parts of triethylamine is then introduced into the mixture. After stirring the mixture for 1 hour at room temperature, 15.9 parts of 2,5-dimethylfuran-3-carboxylic chloride is dripped in. The mixture is then stirred for a further hour and the precipitate is suction filtered, washed with water and then with petroleum ether, and dried. There is obtained 18.2 parts of N-cyclohexyl-2,5-dimethylfuran- 3-hydroxamic acid; m.p.: 135° – 137° C.

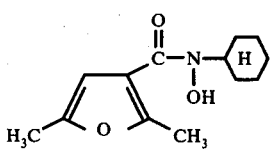

18.2 Parts of N-cyclohexyl-2,5-dimethylfuran-3-hydroxamic acid is dissolved in 100 parts of dichloromethane; a solution of 9.3 parts of sodium hydroxide in 50 parts of water is then added. 19.4 parts of dimethyl sulfate is then dripped into this mixture and the whole is subsequently stirred for 1 hour. The organic phase is separated, washed with water until neutral, dried over anhydrous sodium sulfate and evaporated.

The oil which remains is distilled.

There is obtained 13.9 parts of O-methyl-N-cyclohexyl-2,5-dimethylfuran-3-hydroxamic acid having a boiling point at 0.3 mm Hg of from 133° to 135° C and the refractive index $n_D^{25}$: 1.5068.

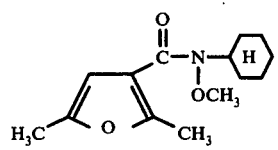

EXAMPLE 3

27.5 Parts of N-cyclopentylhydroxylamine hydrochloride is dissolved in 200 parts of dichloromethane; a solution of 33.6 parts of sodium hydrogen carbonate in 300 parts of water is then added. At room temperature and while stirring thoroughly, 31.8 parts of 2,5-dimethylfuran-3-carboxylic chloride is dripped into this mixture. After stirring the mixture for 1 hour the organic phase is separated, dried over anhydrous sodium sulfate and evaporated. The oil which remains soon solidifies and the crystals obtained are stirred with petroleum ether, suction filtered and dried. There is obtained 14.3 parts of N-cyclopentyl-2,5-dimethylfuran-3-hydroxamic acid having a melting point of from 107° to 109° C.

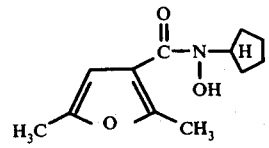

14.3 Parts of N-cyclopentyl-2,5-dimethylfuran-3-hydroxamic acid is dissolved in 100 parts of dichloromethane; to this solution there is added a solution of 7.7 parts of sodium hydroxide in 50 parts of water. 16.1 parts of dimethyl sulfate is then dripped into this mixture. After stirring the mixture for 1 hour, the dichloromethane phase is separated, washed with water until neutral, dried over anhydrous sodium sulfate and evaporated. There is obtained 12.1 parts of O-methyl-N-cyclopentyl-2,5-dimethylfuran-3-hydroxamic acid having a boiling point at 0.1 mm Hg of from 103° to 105° C and the refractive index $N_D^{25}$: 1.5060.

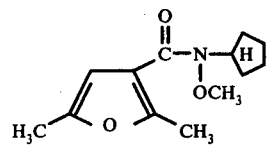

EXAMPLE 4

49 Parts of N-cyclohexylhydroxylamine hydrochloride is dissolved in 400 parts of dichloromethane; at room temperature a solution of 50.4 parts of sodium hydrogen carbonate in 500 parts of water and subsequently 51.6 parts of 2,4,5-trimethylfuran- 3-carboxylic chloride are added to the mixture. After the mixture has been stirred for 2 hours the dichloromethane phase is separated, dried over anhydrous sodium sulfate and evaporated. There is obtained 75 parts of N-cyclohexyl-2,4,5-trimethylfuran-3-hydroxamic acid in the form of an oil. This oil is dissolved in 300 parts of dichloromethane. To this solution there is added 36 parts of sodium hydroxide in 200 parts of water and 75.6 parts of dimethyl sulfate and the whole is stirred for 2 hours. The dichloromethane phase is then separated, washed with water until neutral, dried over anhydrous sodium sulfate and evaporated. Upon distillation of the residue there is obtained 52 parts of O-methyl-N-cyclohexyl-2,4,5-trimethylfuran-3-hydroxamic acid having a boiling point at 0.3 mm Hg of 128° to 130° C and the refractive index $n_D^{25}$: 1.5021.

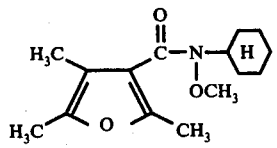

EXAMPLE 5

27.5 Parts of N-cyclopentylhydroxylamine hydrochloride is dissolved in 200 parts of dichloromethane; a solution of 33.6 parts of sodium hydrogen carbonate in 300 parts of water is then added. At room temperature and while stirring thoroughly, 34.5 parts of 2,4,5-trimethylfuran-3-carboxylic chloride is dripped into this mixture. After the mixture has been stirred for 2 hours the dichloromethane phase is separated, dried over anhydrous sodium sulfate and evaporated. There is obtained 36 parts of N-cyclopentyl-2,4,5-trimethylfuran-3-hydroxamic acid in the form of an oil.

This oil is dissolved in 200 parts of dichloromethane; a solution of 18 parts of sodium hydroxide in 100 parts of water and 28.5 parts of dimethyl sulfate are added, and the mixture is stirred for 2 hours. The dichloromethane phase is separated, washed with water until neutral, dried with anhydrous sodium sulfate, evaporated and distilled. There is obtained 25.2 parts of O-methyl-N-cyclopentyl-2,4,5-trimethylfuran-3-hydroxamic acid having a boiling point at 0.2 mm Hg of 116° to 118° C and the refractive index $n_D^{25}$: 1.4992.

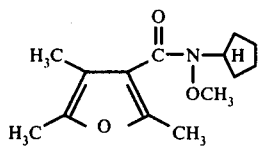

EXAMPLE 6

30 Parts of triethylamine is added to a suspension of 25 parts of N-cyclohexylhydroxylamine hydrochloride in 480 parts of benzene. After the mixture has been stirred for 1 hour, 20 parts of 2,4-dimethylfuran-3-carboxylic chloride is dripped in at room temperature. After the mixture has been stirred for a further 2 hours it is suction filtered, the residue is washed with benzene and the combined benzene phases are washed with water, dried with anhydrous sodium sulfate and evaporated. There is obtained 34 parts of N-cyclohexyl-2,4-dimethylfuran-3-hydroxamic acid in the form of an oil. This oil is dissolved in 370 parts of dichloromethane; at room temperature and while stirring, 18 parts of sodium hydroxide in 70 parts of water, and 28 parts of dimethyl sulfate are added to the solution. After the mixture has been stirred for 1 hour the organic phase is separated, washed with water, dried with sodium sulfate, evaporated and chromatographed using silica gel with a mixture of equal portions of ethyl acetate and cyclohexane. When the eluate is evaporated there is obtained 32 parts of O-methyl-N-cyclohexyl-2,4-dimethylfuran-3-hydroxamic acid having a boiling point at 0.01 mm Hg of 122° to 124° C and the refractive index $n_D^{25}$: 1.5010.

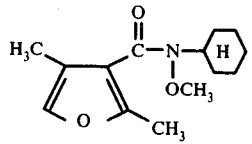

EXAMPLE 7

30 Parts of triethylamine is added to a suspension of 20 parts of N-cyclopentylhydroxylamine hydrochloride in 300 parts of benzene and the whole is stirred for 1 hour. At room temperature, 10 parts of 2-methylfuran-3-carboxylic chloride is dripped in. After the mixture has been stirred for a further 3 hours it is suction filtered, the residue is washed with benzene, and the organic phase is washed with water, dried with sodium sulfate and evaporated. There is obtained 25 parts of N-cyclopentyl-2-methylfuran-3-hydroxamic acid in the form of an oil. This oil is dissolved in 300 parts of dichloromethane; while stirring and at room temperature, 16 parts of sodium hydroxide in 70 parts of water, and 26 parts of dimethyl sulfate are added to the solution. After the mixture has been stirred for 2 hours the organic phase is separated, washed with water until neutral and dried with anhydrous sodium sulfate. Distillation gives 21 parts of O-methyl-N-cyclopentyl-2-methylfuran-3-hydroxamic acid having a boiling point at 0.01 mm Hg of 104° to 108° C and the refractive index $n_D^{25}$: 1.5073.

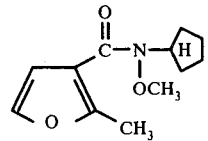

The furanhydroxamic acid derivatives according to the invention have an excellent action on plant-pathogenic fungi. They may be used as foliar and soil fungicides, and especially as seed dressings. As the compounds of the invention are liquids or solids having a low melting point, they may be particularly advantageously used in the form of liquid dressings.

Of special interest is the use of the fungicidal agents for combatting diseases in various crops, especially wheat, rye, barley, oats, rice, Indian corn, cotton, soybeans, beans, coffee, sugar-cane and garden ornamentals.

It should be emphasized that the agents of the invention are effective against fungi of the Basidiomycetes class, e.g., *Tilletia tritici* and *Ustilago tritici* in wheat, *Ustilago hordei* and *Ustilago nuda* in barley, *Ustilago avenae* in oats, *Ustilago maydis* in Indian corn, *Ustilago scitaminea* in sugarcane, *Rhizoctonia solani* in cotton, *Macrophomina phaseoli* in soybeans, *Uromyces fabae* and *Uromyces appendiculatus* in beans, *Sclerotium rolfsii* in lettuce, *Typhula incarnata* in grasses, *Corticium sasakii* in rice, *Hemileia vastatrix* in coffee, and Puccinia types; the compounds are also effective against ligniperdous fungi, e.g., *Coniophora cerebella*, *Merulius lacrimans*, *Coriolus versicolor* and *Lenzites trabea*.

The agents have a systemic action, which is of particular importance in combatting loose and covered smuts in grasses.

The compounds of the invention may be converted into the usual formulations, e.g., solutions, emulsions, suspensions, dusts, powders, pastes and granules. The form of application depends entirely on the purpose for which the active ingredients are being used; in any case a fine and uniform distribution of the active ingredients should be ensured. The formulations are prepared in known manner, e.g., by extending the active ingredients with solvent and/or carriers, with or without emulsifiers and dispersants; when water is used as diluent, other organic solvents may be used as auxiliary solvents. Examples of the main auxiliary substances are solvents such as aromatics (e.g. xylene, benzene), chlorinated aromatics (e.g. chlorobenzenes), paraffins (e.g., petroleum fractions), alcohols (e.g., methanol, butanol), amines (e.g., ethanolamine, dimethylformamide) and water; carriers such as natural rock flours (e.g., kaolins, diatomaceous earth, talc, chalk) and synthetic rock flours (e.g., highly disperse silicic acid, silicates); emulsifiers such as non-ionic and anionic emulsifiers (e.g., polyoxyethylene fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, % by weight of active ingredient.

The formulations and the ready-to-use preparations made therefrom, e.g., solutions, emulsions, suspensions, powders, dusts, pastes and granules, are applied in conventional manner.

Application rates depend on the effect to be achieved and are from 0.2 to 5 and more, but preferably from 0.5 to 2, kg of active ingredient per hectare.

The agents according to the invention may also be mixed and applied with other active ingredients, e.g., herbicides, insecticides, growth regulators, fungicides and fertilizers. When the compounds of the invention are mixed with other fungicides, the fungicidal spectrum is often broadened. In some of these fungicidal compositions synergism is apparent, i.e., the fungicidal action of the composition is greater than that of the sum of the actions of its individual components.

The following list of fungicides with which the compounds of the invention may be combined is intended to illustrate, but not restrict, possible combinations:
dithiocarbamates and derivatives thereof, e.g., ferric dimethyldithiocarbamate (ferbam)
zinc dimethyldithiocarbamate (ziram)
manganese ethylenebisdithiocarbamate (maneb)
zinc ethylenebisdithiocarbamate (zineb)
tetramethylthiuram disulfide (thiram)
manganese-zinc ethylenediamine-bisdithiocarbamate
zinc-(N,N'-propylene-bisdithiocarbamate)
ammonia complex of zinc-(N,N'-ethylene-bisdithiocarbamate) and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
3,5-dimethyl-1,3,5-2H-tetrahydrothiadiazine-2-thione
nitrophenol derivatives, such as
dinitro-(1-methylheptyl)-phenylcrotonate (dinocap)
2-sec-butyl-4,6-dinitrophenyl-3,5-dimethylacrylate (binapacryl)
2-sec-butyl-4,6-dinitrophenylisopropylcarbonate
heterocyclic structures, such as
N-trichloromethylthiotetrahydrophthalimide (captan)
N-trichloromethylthiophthalimide (folpet)
N-(1,1,2,2-tetrachloroethylthio)-tetrahydrophthalimide
N,N-dimethyl-N-phenyl-(N-fluorodichloromethylthio)-sulfamide
N-methyl-N-phenyl-(N'-fluorodichloromethylthio)-N'-methylsulfamide
2-heptadecyl-2-imidazoline (glyodin)
2,4-dichloro-6-(o-chloroanilino)-s-triazine
diethylphthalimidophosphorothioate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone (dithianon)
2-thio-1,3-dithio-[4,5-b]-quinoxaline (thioquinox)
methyl 1-(butylcarbamoyl)-2-benzimidazolecarbamate
2-methoxycarbonylaminobenzimidazole
2-thiocyanomethylthiobenzothiazole (busan)
4-(2-chlorophenylhydrazono)-3-methyl-5-isooxazolone
pyridine-2-thiol-1-oxide
8-hydroxyquinoline and its copper salt
5-methyl-5-vinyl-3-(3,5-dichlorophenyl)-2,4-dioxo-1,3-oxazolidine
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene (thiophanat)
1,2-bis-(3-methoxycarbonyl)-2-thioureido)-benzene
and various fungicides, such as
dodecylguanidine acetate (dodine)
3-[2-(3,5-dimethyl-2-oxycyclohexyl)-2-hydroxyethyl]-glutarimide (cycloheximide)
hexachlorobenzene
N-dichlorofluoromethyl-N',N'-dimethyl-N-phenylsulfuric acid diamide
2,6-dimethyl-N-tridecylmorpholine and its salts
2,6-dimethyl-N-cyclododecylmorpholine and its salts
1-(3,4-dichloroanilino)-1-formylamino-2,2,2-trichloroethane
2,3-dichloro-1,4-naphthoquinone
2-thiocyanomethylthiobenzothiazole
1,4-dichloro-2,5-dimethoxybenzene
p-dimethylaminobenzenediazosodium sulfonate
2-chloro-1-nitropropane
polychloronitrobenzenes, such as pentachloronitrobenzene, methyl isothiocyanate, fungicidal antibiotics such as griseofulvin and kasugamycin, tetrafluorodichloroacetone, 1-phenylthio semicarbazide, Bordeaux mixture, nickel-containing compounds and sulfur.

Of particular importance is admixture with fungicides having an especially good helminthosporium action.

The following active ingredients have proved to be particularly suitable for combinations:

manganese ethylenebisdithiocarbamate
manganese-zinc-ethylenediamine-bisdithiocarbamate
tetramethylthiuram disulfide
methyl 1-(butylcarbamoyl)-2-benzimidazole carbamate
2-methoxycarbonylaminobenzimidazole
1,4-dichloro-2,5-dimethyloxybenzene
N-trichloromethylthiotetrahydrophthalimide
N-trichloromethylthiophthalimide
N-(1,1,2,2-tetrachloroethylthio)-tetrahydrophthalimide
5-ethoxy-3-trichloromethyl-1,2,4-thiadiazole
2-thiocyanomethylthiobenzothiazole
8-hydroxyquinoline and its copper salt
2-(2'-furyl)-benzimidazole
2-(4-thiazolyl)-benzimidazole
N-(3,5-dichlorophenyl)-succinimide
2,6-dichloro-4-nitroaniline
hexachlorobenzene
1-(2-(2,4-dichlorophenyl)-2-(2-propenoxy)-ethyl)-H-imidazole.

These agents may be added (if desired, immediately before use (tankmix)) to the fungicides of the invention in a weight ratio of from 1:10 to 10:1.

The following examples illustrate the biological action of the hydroxamic acid derivatives according to the invention.

EXAMPLE 8

100 g samples of winter barley seed ("Astrix" variety) naturally infected with loose smut (*Ustilago nuda*) are carefully treated in glass bottles for 5 minutes with 200 mg (=0.2 wt%) of the following dressings. During the treatment the bottles are shaken and care is taken that the surface of the seeds is uniformly covered with dressing.

Three 15 g samples of the treated seeds are compared with the same amounts of untreated seeds in the open by sowing them in rows in 3 plots, each 1 m² in size. The seeds are sown in October; after six months the smut has spread in the untreated control plots to such an extent that it is possible to assess the effectiveness of the fungicides.

| Active ingredient | Amount of active ingredient in dressing in % | Fungus attack in % |
|---|---|---|
| 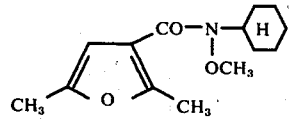 | 40 | 0 |
| control (untreated) | — | 13.8 |

EXAMPLE 9

100 g samples of winter wheat seed of the "Jubilar" variety are artificially infected by placing them in glass bottles containing 200 mg of spores of wheat smut (*Tilletia tritici*) and carefully shaking the bottles for 5 minutes. The seeds are then similarly treated with 200 mg (0.2%) of the dressings listed below. Care is taken that the surface of the seeds is uniformly coated with the dressings.

Three 15 g samples of the treated seeds are compared with the same amounts of untreated seeds in the open by sowing each of the three samples in rows on 1 m² plots. The seeds are sown at the beginning of November; after 8 months, the ears of wheat in the untreated control plots are so badly afflicted by symptoms of the disease that it is possible to evaluate the experiment.

| Active ingredient | Amount of active ingredient in dressing in % | Fungus attack in % |
|---|---|---|
| 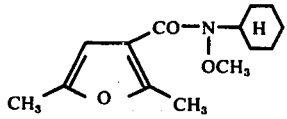 | 40 | 0.2 |
| 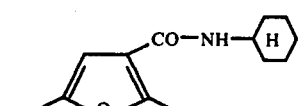 prior art (German Laid-Open Application 2,019,535) | 40 | 0.6 |
| 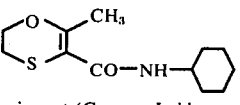 prior art (German Laid-Open Application 1,567,211) | 40 | 1.1 |
| control (untreated) | — | 62.4 |

EXAMPLE 10

Leaves of pot-grown bean plants of the "Mombacher Speck" variety are artificially infected with spores of bean rust (*Uromyces fabae*) and oat plants of the "Flamingskrone" variety with spores of crown rust of oats (*Puccinia coronata*) and both sets of plants placed for 24 hours in a steam-saturated chamber at 20° to 25° C. The plants are then sprayed with aqueous spray liquors which contain (dissolved or emulsified in water) a mixture of 80% of the active ingredient under examination and 20% of lignin sulfate, and placed in a greenhouse at a temperature of from 20° to 22° C and having a relative humidity of from 75 to 80%. After 10 days the extent of fungus spread is assessed.

| Active ingredient | Extent of fungus attack after spraying with liquor containing 0.1% of active ingredient | |
|---|---|---|
| | bean rust | crown rust |
| 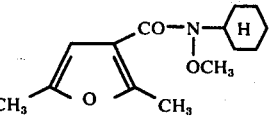 | 0 | 1 |
| 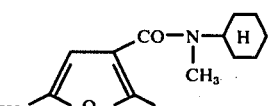 prior art (German Laid-Open Application 2,019,535) | 2 | 5 |
| control (untreated) | 5 | 5 |

0 = no attack, graduated down to
5 = total affliction (surface of leaves completely covered by fungus)

EXAMPLE 11

Cotton seeds of the "Delta Pine" variety are thoroughly dusted with a triturated dressing containing 40 wt% of the active ingredient under investigation and 60% of talc, in amounts of 0.3 g per 100 g of seed. The cotton seeds prepared in this manner are then placed in pots and covered with soil which has previously been artificially infected with the fungus *Rhizoctonia solani*. After 21 days the results obtained are compared with those obtained with a prior art fungicide and in the untreated control.

| Active ingredient | Percentage of diseased cotton plants 21 days after emergence |
|---|---|
| 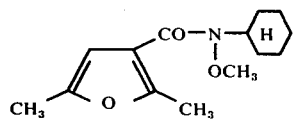 | 0 |
| 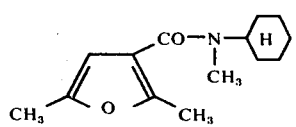<br>prior art (German Laid-Open Application 2,019,535) | 30 |
| control (untreated) | 90 |

EXAMPLE 12

Filter paper discs having a diameter of 13 mm and a thickness of 1 mm are impregnated with 0.1 ml solutions containing 6.25, 12.5, 25, 50 and 100 parts of active ingredient per million parts of solution. The discs are then placed on a nutrient agar containing 5% malt and which has been inoculated with spores of sugarcane smut (*Ustilago scitaminea*). The Petri dishes containing the agar are then incubated for 24 hours at 30° C. After this time the spores in the untreated control dishes have germinated; the fungicidal action of the active ingredients is assessed by means of the haloes which have formed round the discs. The halo radius is obtained by subtracting 13 mm from the overall diameter and dividing the remainder by two.

In the table the figures relate to the halo radius in mm and have the following meanings:

26 – 18 excellent action
17 – 13 good action
12 – 4 fair action
3 – 1 very poor action
0 ineffective Diffusion test to determine
the fungicidal action
on *Ustilago scitaminea*

Amount of active ingredient in
the impregnating solution
in ppm

| Active ingredient | 6.25 | 12.5 | 25 | 50 | 100 |
|---|---|---|---|---|---|
| 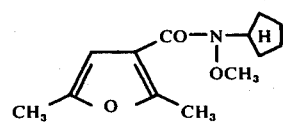 | 6 | 9 | 13 | 18 | 26 |
| 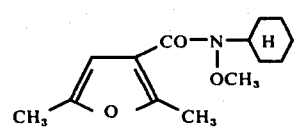 | 11 | 16 | 18 | 21 | 26 |
| 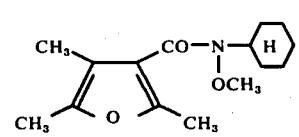 | 0 | 0 | 0 | 6 | 11 |

26 – 18 excellent action
17 – 13 good action
12 – 4 fair action
3 – 1 very poor action
0 ineffective Diffusion test to determine
the fungicidal action
on *Ustilago scitaminea*

Amount of active ingredient in
the impregnating solution
in ppm

| Active ingredient | 6.25 | 12.5 | 25 | 50 | 100 |
|---|---|---|---|---|---|
| 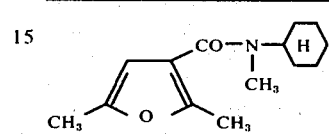<br>prior art (German Laid-Open Application 2,019,535) | 0 | 0 | 0 | 2 | 6 |
| control (untreated) | 0 | 0 | 0 | 0 | 0 |

EXAMPLE 13

100 g samples of barley seed under heavy attack from the fungus *Helmiathosporium sativum* are shaken in glass bottles for about 5 minutes with 300 mg (= 0.3 wt%) of the following dressings or dressing compositions. After this time the dressings are uniformly distributed on the surface of the barley seeds. Ten seeds treated in this manner are then placed with a pair of tweezers on a 2% malt extract agar in Petri dishes; for each series of experiments a total of 10 dishes is used. The dishes are then kept at from +80° to +10° C for a week. The seeds under fungus attack are then counted. The fungus afflicting the seeds is usually *Helminthosporium sativum;* other fungi, e.g., Alternaria and Penicillium, are also registered.

| Active ingredient | Amount of active ingredient in dressing in % | Fungus attack in % |
|---|---|---|
| 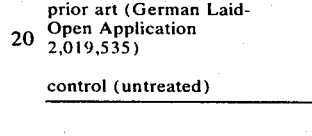 (I) | 50 | 24 |
| manganese ethylene (II) bisdithiocarbamate prior art (U.S. Pat. No. 2,504,404) | 32 | 6 |
| composition of I and II | 50 + 32 | 0 |
| 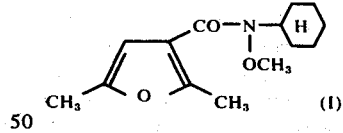<br>III<br>prior art (German Printed Application 1,812,206) | 20 | 18 |
| composition of I, II and III | 50 + 20 + 20 | 0 |
| 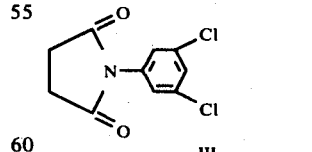<br>IV | 10 | 15 |

| Active ingredient | Amount of active ingredient in dressing in % | Fungus attack in % |
|---|---|---|
| composition of I and IV | 50 + 10 | 0 |
| control (untreated) | | 86 |

EXAMPLE 14

90 Parts by weight of the compound of Example 1 is mixed with 10 parts by weight of N-methyl- -pyrrolidone. A mixture is obtained which is suitable for application in the form of very fine drops.

EXAMPLE 15

20 Parts by weight of the compound of Example 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 16

20 Parts by weight of the compound of Example 3 is dissolved in a mixture consisting of 40 parts by weight of cyclohexanone, 30 parts by weight of isobutanol, 20 parts by weight of the adduct of 7 moles of ethylene oxide to 1 mole if isooctylphenol, and 10 parts by weight of the adduct of 40 moles of ethylene oxide to 1 mole of caster oil. By pouring the solution into 100,000 Parts by weight of water and uniformly distributing it therein, an aqueous dispersion is obtained containing 0.02% by weight of the active ingredient.

EXAMPLE 17

20 Parts by weight of compound I from Example 13 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 18

20 Parts by weight of compound I from Example 13 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 19

3 Parts by weight of compound I from Example 13 is intimately mixed with 97 parts by weight of particulate kaolin. A dust is obtained containing 3% by weight of the active ingredient.

EXAMPLE 20

30 Parts by weight of compound I from Example 13 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. A furanhydroxamic acid derivative of the formula

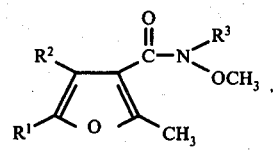

where $R^1$ denotes hydrogen or methyl, $R^2$ denotes hydrogen or methyl and $R^3$ denotes cyclopentyl or cyclohexyl.

2. A process for combatting fungi wherein the objects to be protected against fungus infection are treated with an effective amount of a furanhydroxamic acid derivative of the formula

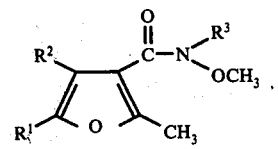

where $R^1$ denotes hydrogen or methyl, $R^2$ denotes hydrogen or methyl and $R^3$ denotes cyclopentyl or cyclohexyl.

3. O-methyl-N-cyclohexyl-2,5-dimethylfuran-3-hydroxamic acid.

4. O-methyl-N-cyclopentyl-2,5-dimethylfuran-3-hydroxamic acid.

5. O-methyl-N-cyclohexyl-2,4,5-trimethylfuran-3-hydroxamic acid.

* * * * *